United States Patent [19]

Rolf et al.

[11] 4,288,362

[45] Sep. 8, 1981

[54] MONOAZO PIGMENTS CONTAINING A QUINAZO LINONYLACETOACETANILIDE COUPLING COMPONENT

[75] Inventors: Meinhard Rolf; Rütger Neeff; Walter Müller, all of Leverkusen, Fed. Rep. of Germany

[73] Assignee: Bayer Aktiengesellschaft, Leverkusen, Fed. Rep. of Germany

[21] Appl. No.: 43,494

[22] Filed: May 29, 1979

[30] Foreign Application Priority Data

Jul. 12, 1978 [DE] Fed. Rep. of Germany ....... 2830555

[51] Int. Cl.³ .................... C09B 29/01; C09B 29/32; D06P 1/642; D06P 5/06
[52] U.S. Cl. .................... 260/154; 106/23; 106/288 Q; 106/300; 106/308 Q; 260/37 NP; 260/37 N; 260/37 PC; 260/40 R; 260/40 TN; 260/42.21; 544/248; 544/283
[58] Field of Search ......................... 260/154, 146 D

[56] References Cited

U.S. PATENT DOCUMENTS

| | | | |
|---|---|---|---|
| 3,609,134 | 9/1971 | Mory | 260/152 |
| 3,711,461 | 7/1973 | Pretzer et al. | 260/154 |
| 3,963,694 | 6/1976 | Mory et al. | 260/154 |
| 4,052,377 | 10/1977 | Junge et al. | 260/154 |

FOREIGN PATENT DOCUMENTS 2451097  5/1975  Fed. Rep. of Germany ...... 260/154

*Primary Examiner*—Floyd D. Higel
*Attorney, Agent, or Firm*—Sprung, Felfe, Horn, Lynch & Kramer

[57] ABSTRACT

Heterocyclic compounds of the formula wherein
$R_1$ denotes a substituent,
$R_2$ denotes an optionally substituted carbocyclic-aromatic or heterocyclic-aromatic radical and
n denotes 0, 1, 2, 3 or 4, and azo colorants of the formula wherein
D denotes the radical of an aromatic or hetero-aromatic amine which is free from sulphonic acid groups,
p denotes an integer, preferably 1 or 2, and
$R_1$, $R_2$ and n have the meaning mentioned in claim 1, processes for the preparation of the heterocyclic compounds and of the azo colorants, and the use of the azo colorants as pigments.

4 Claims, No Drawings

MONOAZO PIGMENTS CONTAINING A QUINAZO LINONYLACETOACETANILIDE COUPLING COMPONENT

The invention relates to heterocyclic compounds of the formula

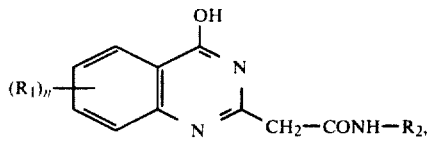

processes for their preparation, their use as coupling components for azo colorants, and the azo pigments prepared therefrom.

In the formula I, $R_1$ denotes a substituent, $R_2$ denotes an optionally substituted carbocyclic-aromatic or heterocyclic-aromatic radical and n denotes 0, 1, 2, 3 or 4.

Preferentially suitable substituents $R_1$ are halogen, especially chlorine and bromine, alkyl, especially $C_1$-$C_4$-alkyl, nitro, alkylsulphonylamino, especially $C_1$-$C_4$-alkylsulphonylamino, and alkylcarbonylamino, especially ($C_1$-$C_4$-alkyl-)carbonylamino. Further suitable substituents $R_1$ are, for example $C_1$-$C_4$-alkoxy, trifluoromethyl, phthalimidyl, carboxyl, cyano and optionally substituted carbamoyl, sulphamoyl, benzoylamino, arylamino and arylsulphonylamino radicals.

Preferred possible substituents of the carbamoyl and sulphamoyl groups are $C_1$-$C_4$-alkyl, phenyl which is optionally substituted by $C_1$-$C_4$-alkyl, $C_1$-$C_4$-alkoxy, fluorine, chlorine, bromine, phthalimidyl or nitro, and benzyl.

Benzoylamino is optionally substituted in the benzene nucleus by chlorine, $C_1$-$C_4$-alkyl, $C_1$-$C_4$-alkoxy or nitro. Arylamino is, in particular, phenylamino which is optionally substituted by $C_1$-$C_4$-alkyl, $C_1$-$C_4$-alkoxy, fluorine, chlorine, bromine or nitro.

Optionally substituted arylsulphonylamino preferentially denotes phenylsulphonylamino which is substituted by $C_1$-$C_4$-alkyl, $C_1$-$C_4$-alkoxy, fluorine, chlorine, bromine and nitro.

$R_2$ preferably denotes optionally substituted phenyl, for example phenyl which can carry 1-5 substituents, such as chlorine, bromine, fluorine, $C_1$-$C_4$-alkyl, $C_1$-$C_4$-alkoxy, nitro, trifluoromethyl, cyano, carboxyl, $C_1$-$C_4$-alkoxycarbonyl; optionally substituted carbamoyl and sulphamoyl radicals, phthalimidyl, acylamino, arylamino, alkylsulphonylamino or arylsulphonylamino radicals or a radical of the formula

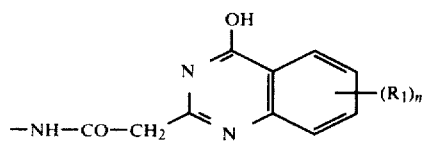

where $R_1$ and n have the abovementioned meaning.

Suitable substituents of the carbamoyl, sulphamoyl, acylamino, arylamino, alkylsulphonylamino and arylsulphonylamino radicals are those already mentioned in the case of $R_1$.

$R_2$ furthermore represents optionally substituted polynuclear and aromatic and/or heterocyclic radicals, such as α-naphthyl, β-naphthyl, α-anthraquinonyl, β-anthraquinonyl, α-pyridyl, 2-benzthiazyl or 5-benzimidazolonyl.

n preferably represents 0, 1 or 2.

The heterocyclic compounds of the formula I are prepared by reaction of aromatic amines of the formula $$R_2-NH_2$$

wherein $R_2$ has the abovementioned meaning, with functional derivatives of quinazolinonyl-acetic acid.

Suitable derivatives of quinazolinonyl-acetic acid are, in particular, the halides, above all the chloride, the alkyl esters of the formula (III)

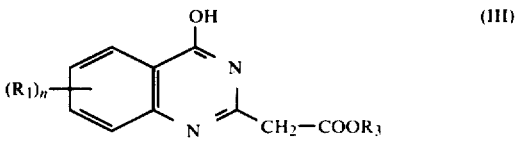

wherein $R_3$ represents $C_1$-$C_4$-alkyl and $R_1$ and n have the abovementioned meaning, the iminoalkyl esters and the nitrile.

The reaction is carried out at 120°-220° in bulk or in an inert organic solvent, such as o-dichlorobenzene, 1,2,4-trichlorobenzene, ethylene glycol dimethyl ether, ethylene glycol diethyl ether, xylene or nitrobenzene.

The compounds of the formula I are suitable for use as coupling components for the preparation of azo colorants, especially for the preparation of azo pigments.

Hence, the invention further relates to azo colorants of the formula

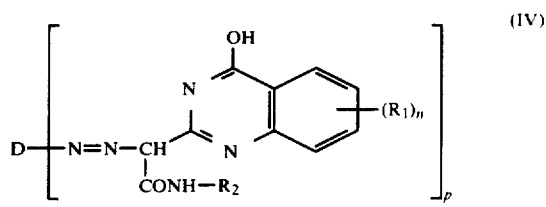

wherein

D denotes the radical of an aromatic or hetero-aromatic amine which is free from sulphonic acid groups and p denotes an integer, preferably 1 or 2 and $R_1$, $R_2$ and n have the abovementioned meaning.

Examples of suitable diazo components are aniline, 2-methylaniline, 2,4-dimethylaniline, 2-nitroaniline, 3-nitroaniline, 4-nitroaniline, 2,4-dinitroaniline, 2-chloro-4-nitroaniline, 4-chloro-2-nitroaniline, 2-chloro-5-nitroaniline, 2-nitro-4-methylaniline, 2-methyl-4-nitroaniline, 2-methyl-5-nitroaniline, 4-methoxy-2-nitroaniline, 2-cyano-4-nitroaniline, 2-bromo-4-nitroaniline, 2-nitro-4-methylsulphonylaniline, 2-nitro-4-ethylsulphonylaniline, 2-chloroaniline, 4-chloroaniline, 2,4-dichloroaniline, 2,5-dichloroaniline, 2,6-dichloroaniline, 3,4-dichloroaniline, 3,5-dichloroaniline, 2,4,5-trichloroaniline, 2,4,6-trichloroaniline, 2-cyano-5-chloroaniline, 2-methyl-4-chloroaniline, 2-methyl-5-chloroaniline, 2,4-dichloro-5-ethylaniline, 2,5-dichloro-4-methylaniline, 2-chloro-4-methylsulphonylaniline, 2-cyano-5-chloroaniline, 2,4-dichloro-5-methoxyaniline, 2-chloro-5-trifluoromethylaniline, 4-chloro-2-trifluoromethylaniline, 3,5-bis-trifluoromethylaniline, 2,4- dimethoxyaniline, 2,5-dimethoxyaniline, 2,5-diethoxyaniline, 2,4-dimethoxy-5-chloroaniline, 2,5-dimethoxy-4-chloroaniline, 2-methoxy-5-methylaniline, 4-methoxy-2-methylaniline, 2-methoxy-5-methyl-4-chloroaniline, 2-methoxy-4-nitroaniline, 4-methoxy-2-nitroaniline, 2-methoxy-5-nitroaniline, 2,5-dimethoxy-4-nitroaniline, 2-methoxy-5-methyl-4-nitroaniline, 2-methoxy-5-chloro-4-nitroaniline, 2-methoxy-5-ethylsulphonylaniline, 2-methoxy-5phenylsulphonylaniline, 2-methoxy-5-benzylsulphonylaniline, 2-methoxy-4-chloroaniline, 2-ethoxy-4-chloroaniline, 2-methoxy-5-chloroaniline, 2-ethoxy-5-chloroaniline, 2-methoxy-4,5-dichloroaniline, 2-amino-5-chlorodiphenyl ether, 2-amino-4,4'-dichlorodiphenyl ether, 2-amino-4,6-dichlorodiphenyl ether, 4-amino-5-methoxybenzenesulphonic acid 4-nitrophenyl ester, 5-acetylamino-2-nitroaniline, 5-acetylamino-2-chloro-5-methylaniline, 4-acetylamino-2,5-dichloroaniline, 5-acetylamino-2,4-dichloroaniline, 4-benzoylamino-2-methyl-5-methoxyaniline, 5-benzoylamino-2-chloroaniline, 4-benzoylamino-2-chloro-5-methoxyaniline, 2-amino-benzoic acid methyl ester, 2-aminobenzoic acid ethyl ester, 2-aminobenzoic acid isobutyl ester, 4-chloro-2-aminobenzoic acid methyl ester, 5-chloro-2-aminobenzoic acid methyl ester, 6-chloro-2-aminobenzoic acid methyl ester, 3,5-dichloro-2-aminobenzoic acid methyl ester, 4,6-dichloro-2-aminobenzoic acid methyl ester, 5-bromo-2-aminobenzoic acid methyl ester, 4-nitro-2-aminobenzoic acid methyl ester, 5-nitro-2-aminobenzoic acid methyl ester, 4-methyl-2-aminobenzoic acid methyl ester, 5-methyl-2-aminobenzoic acid methyl ester, 6-methyl-2-aminobenzoic acid methyl ester, 4-trifluoromethyl-2-aminobenzoic acid methyl ester, 4-methoxy-2-aminobenzoic acid methyl ester, 4-methoxy-3-aminobenzoic acid phenyl ester, 4-carbamoyl-2-aminobenzoic acid methyl ester, 4-acetylamino-2-aminobenzoic acid methyl ester, 4-benzoylamino-2-aminobenzoic acid methyl ester, 4-(2,5-dichlorobenzoylamino)-2-aminobenzoic acid methyl ester, 4-sulphamoyl-2-aminobenzoic acid methyl ester, 2-aminonaphthalene-3-carboxylic acid methyl ester, 4-methyl-3-aminobenzoic acid methyl ester, 1-aminobenzene-2,5-dicarboxylic acid dimethyl ester, 1-aminobenzene-3,5-dicarboxylic acid dimethyl ester, 2-aminobenzamide, 4-aminobenzamide, 4-chloro-3-aminobenzamide, 4,6-dichloro-3-aminobenzamide, 3-amino-4-methoxy-benzamide, 3-amino-4-methoxybenzoic acid phenylamide, 3-amino-4-methylbenzoic acid methylamide, 3-amino-4-methylbenzoic acid 2,4-dimethylphenylamide, 1-aminobenzene-3,5-dicarboxylic acid diamide, 3-amino-4-methylbenzoic acid 2,5-dichlorophenylamide, 3-amino-4-methoxycarbonylbenzamide, 3-amino-4-methoxycarbonylbenzoic acid phenylamide, 3-amino-4-methoxycarbonylbenzoic acid 2,5-dichlorophenyl-amide, 3-amino-4-methoxybenzenesulphonic acid methylamide, 3-amino-4-methoxybenzenesulphonic acid diethylamide, 2,5-dimethoxy-4-aminobenzenesulphonic acid methylamide, 2-methyl-5-methoxy-4-aminobenzenesulphonic acid methylamide, 3-amino-4-methylbenzenesulphonic acid phenylamide, 4-amino-2,5-dimethoxybenzenesulphonic acid methylamide, 4-amino-2-methyl-5-methoxybenzenesulphonic acid methylamide, 2-chloro-1-aminonaphthalene, 1-amino-2-methoxynaphthalene, 1-amino-4-nitro-naphthalene, 2-amino-5-nitronaphthalene, 2-aminothiazole, 2-amino-4-methylthiazole, 2-amino-5-chlorothiazole, 2-amino-5-nitrothiazole, 2-amino-4-methylthiazole-5-carboxylic acid methyl ester, 2-amino-4-methylthiazole-5-carboxylic acid dimethylamide, 2-aminobenzthiazole, 2-amino-6-methylbenzthiazole, 2-amino-5-methoxybenzthiazole, 2-amino-6-methoxybenzthiazole, 2-amino-6-chlorobenzthiazole, 2-amino-6-methylsulphonylbenzthiazole, 6-methyl-2-(4-aminophenyl)-benzthiazole, 5-amino-3-phenyl-1,2,4-thiadiazole, 2-amino-4-methylcarbostyril, 6-amino-4-methyl-2-chlorocarbostyril, 3-amino-4-methoxybenzoxazole, 6-amino-2,4-dihydroxyquinazoline, 1-aminoanthraquinone, 2-aminoanthraquinone, 1-amino-2-chloroanthraquinone, 1-amino-4-chloroanthraquinone, 1-amino-5-chloroanthraquinone, 1-amino-6-chloroanthraquinone, 1-amino-6(7)-chloroanthraquinone (mixture), 1-amino-5,8-dichloroanthraquinone, 1-amino-2-bromoanthraquinone, 1-amino-2,4-dibromoanthraquinone, 1-amino-6,7-dichloroanthraquinone, 1-amino-6-fluoroanthraquinone, 1-amino-7-fluoroanthraquinone, 1-amino-6,7-difluoroanthraquinone, 2-amino-1-chloroanthraquinone, 2-amino-3-chloroanthraquinone, 2-amino-3-bromoanthraquinone, 1-amino-4-nitroanthraquinone, 1-amino-5-nitroanthraquinone, 1-amino-2-methylanthraquinone, 1-amino-2-methyl-4-chloroanthraquinone, 1-amino-2-methyl-4-bromoanthraquinone, 1-aminoanthraquinone-2-carboxylic acid, 1-aminoanthraquinone-2-carboxylic acid amide, 1-aminoanthraquinone-2-carboxylic acid methyl ester, 1-amino-4-nitroanthraquinone-2-carboxylic acid, 1-amino-2-acetylanthraquinone, 1-amino-4-acetylaminoanthraquinone, 1-amino-5-acetylaminoanthraquinone, 1-amino-5-benzoylaminoanthraquinone, 1-amino-4-benzoylaminoanthraquinone, 1-amino-8-benzoylaminoanthraquinone, 1-amino-4-hydroxyanthraquinone, 1-amino-5-hydroxyanthraquinone, 1-amino-4-methoxyanthraquinone, 1-amino-2-methoxy-4-hydroxyanthraquinone, 1-amino-4-methylaminoanthraquinone, 1-amino-4-benzylaminoanthraquinone, 1-amino-4-cyclohexylaminoanthraquinone, 1-amino-4-anilinoanthraquinone, 1-amino-2-bromo-4-methylmercaptoanthraquinone, 1-amino-4-(4-methylphenylsulphonylamino)-2-phenylthioanthraquinone, 1-amino-6-methylmercaptoanthraquinone, 2-phenyl-6-amino-4,5-phthaloylbenzimidazole, 6-chloro-2-amino-3,4-phthaloylacridone, 7-chloro-2-amino-3,4-phthaloylacridone, 5-chloro-8-amino-3,4-phthaloylacridone, 3-aminobenzanthrone, 5-aminopyrazoleanthrone, 4-aminoanthrapyrimidine, 6-aminoanthrapyrimidine, 6-amino-3-methylanthrapyridone, 7-amino-3-methylanthrapyridone, 1,5-diaminoanthraquinone, 1,4-diaminoanthraquinone, 1,8-diaminoanthraquinone, 1,6-/1,7-diaminoanthraquinone (mixture), 2,6-diaminoanthraquinone, 1,5-diamino-4-chloroanthraquinone, 1,4-diamino-5-nitroanthraquinone, 1,5-diamino-2,4,6,8-tetrabromoanthraquinone, 1,5-diamino-4,8-dihydroxyanthraquinone, 1,8-diamino-4,5-dihydroxyanthraquinone, 4,4'-diamino-1,1'-dianthrimide and 1-amino-2-bromo-4-(4-methylphenylsulphonylamino)-anthraquinone.

Preferred diazo components are those of the benzene and anthraquinone series.

Particularly preferred dyes are those of the formula

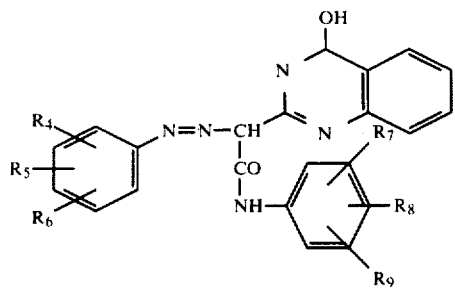

wherein

R$_4$ represents hydrogen, halogen, such as fluorine, chlorine and bromine, C$_1$-C$_4$-alkyl, C$_1$-C$_4$-alkoxy, nitro, cyano, carboxyl, C$_1$-C$_4$-alkylsulphonyl, trifluoromethyl, C$_1$-C$_4$-alkylcarbonylamino, benzoylamino which is optionally substituted by C$_1$-C$_4$-alkyl, C$_1$-C$_4$-alkoxy, fluorine, chlorine, bromine or nitro, C$_1$-C$_4$-alkoxycarbonyl, carbamoyl or sulphamoyl which are optionally monosubstituted or disubstituted by C$_1$-C$_4$-alkyl, phenyl or benzyl, it being possible for phenyl and benzyl to be further substituted by C$_1$-C$_4$-alkyl, C$_1$-C$_4$-alkoxy, fluorine, chlorine, bromine and nitro, C$_1$-C$_4$alkylsulphonylamino, and phenylsulphonylamino which is optionally substituted by C$_1$-C$_4$-alkyl, C$_1$-C$_4$-alkoxy, fluorine, chlorine, bromine or nitro, R$_5$ represents hydrogen, halogen, such as fluorine, chlorine and bromine, C$_1$-C$_4$-alkyl, cyano, C$_1$-C$_4$-alkoxy, nitro or trifluoromethyl, R$_6$ represents hydrogen, chlorine, C$_1$-C$_4$-alkyl or C$_1$-C$_4$-alkoxy, R$_7$ represents hydrogen, halogen, such as fluorine, chlorine and bromine, C$_1$-C$_4$-alkyl, C$_1$-C$_4$-alkoxy, nitro, cyano, C$_1$-C$_4$-alkylsulphonyl, trifluoromethyl, C$_1$-C$_4$-alkylcarbonylamino, benzoylamino which is optionally substituted by C$_1$-C$_4$-alkyl, C$_1$-C$_4$-alkoxy, fluorine, chlorine, bromine or nitro, C$_1$-C$_4$-alkoxycarbonyl, or carbamoyl or sulphamoyl which are optionally monosubstituted or disubstituted by C$_1$-C$_4$-alkyl, phenyl or benzyl, it being possible for phenyl and benzyl to be further substituted by C$_1$-C$_4$-alkyl, C$_1$-C$_4$-alkoxy, fluorine, chlorine, bromine and nitro, R$_8$ represents hydrogen, halogen, such as fluorine, chlorine or bromine, C$_1$-C$_4$-alkyl, cyano, C$_1$-C$_4$-alkoxy, nitro or trifluoromethyl and R$_9$ represents hydrogen, chlorine, C$_1$-C$_4$-alkyl, C$_1$-C$_4$-alkoxy or a radical of the formula

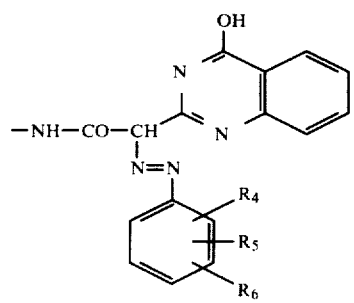

wherein R$_4$, R$_5$ and R$_6$ have the abovementioned meanings.

Further preferred dyes are those of the formula

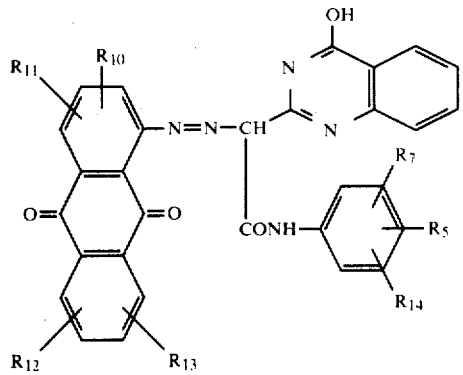

wherein

R$_7$ and R$_8$ have the abovementioned meaning and

R$_{10}$, R$_{11}$, R$_{12}$ and R$_{13}$ represent hydrogen, chlorine, bromine, carboxyl, C$_1$-C$_4$-alkoxycarbonyl, carboxamide, C$_1$-C$_4$-alkylcarbonylamino, benzoylamino which is optionally substituted by 1 or 2 nitro or 1 to 5 chlorine or bromine, C$_1$-C$_4$-alkylsulphonylamino or phenylsulphonylamino which is optionally substituted by methyl, methoxy or chlorine, and R$_{14}$ represents hydrogen, chlorine, C$_1$-C$_4$-alkyl, C$_1$-C$_4$-alkoxy or the radical of the formula

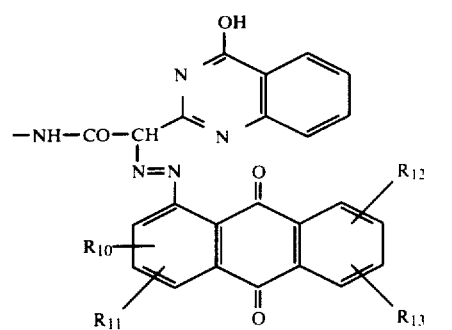

wherein R$_{10}$-R$_{13}$ have the abovementioned meanings.

The azo colorants IV are prepared by coupling diazotised aromatic amines of the formula $$D-(NH_2)_p \qquad (IX)$$

wherein D and p have the abovementioned meanings, with the heterocyclic compounds I.

Several methods can be used for the coupling reactions:

(1) The coupling component is dissolved or suspended in alkali, the solution or suspension is brought to a suitable pH value and an acid solution or suspension of a diazonium salt is added. The mixture is stirred until the reaction has ended and the dye is purified, if necessary, by heating in an organic solvent, such as n-butanol, toluene, chlorobenzene, pyridine, nitrobenzene, o-dichlorobenzene, 1,2,4-trichlorobenzene, tetramethylenesulphone, dimethylformamide, N-methylpyrrolidone, ethylene glycol dimethyl ether or ethylene glycol diethyl ether.

(2) The diazo component IX, in an organic solvent such as dimethylformamide, dimethylacetamide, dimethylsulphoxide, tetramethylenesulphone, tetraphenylurea, N-methylpyrrolidone, nitrobenzene, o-dichlorobenzene, 1,2,4-trichlorobenzene, ethylene glycol dimethyl ether, ethylene glycol diethyl ether or acetic acid, is diazotised, in the presence of an acid such as sulphuric acid, phosphoric acid, benzenesulphonic acid, ethanesulphonic acid, p-toluenesulphonic acid, naphthalene-2,6-disulphonic acid, formic acid, acetic acid, dichloroacetic acid, 2,4-dichlorobenzoic acid, oxalic acid, succinic acid, maleic acid, tartaric acid or terephthalic acid, with organic nitrites such as methyl nitrite, ethyl nitrite, iso-amyl nitrite or, advantageously, nitrites of glycols and glycol derivatives, such as methoxyethyl nitrite or ethoxyethyl nitrite, or with alkali metal nitrites, such as sodium nitrite. A suspension of the coupling component, advantageously in the same solvent, is then stirred into the mixture. After completion of coupling, the crude product is purified by raising the temperature in the coupling solution to 90°-200° C., and is isolated by filtering off.

The second process can also be varied in that the diazo component and coupling component are initially introduced into the organic solvent and the alkyl nitrite or alkali metal nitrite is added, so that diazotisation and coupling take place simultaneously. This process variant, again, is advantageously followed by a heat treatment to purify the pigment thus prepared.

The azo colorants of the formula IV are obtained in a form suitable for pigments or can be converted to the suitable form by after-treatment methods which are in themselves known, for example by dissolving or swelling in strong inorganic acids, such as sulphuric acid, and pouring out onto ice. The finely divided state can also be achieved by grinding with or without grinding auxiliaries such as inorganic salts or sand, optionally in the presence of solvents such as toluene, xylene, dichlorobenzene or N-methylpyrrolidone. The tinctorial strength and transparency of the pigment can be influenced by varying the after-treatment.

Because of their fastness to light and to migration, the pigments of the formula IV are suitable for a great diversity of pigment applications. Thus, they can be used for the preparation of very fast-pigmented systems, such as mixtures with other materials, formulations, paints, printing inks, coloured paper and coloured macromolecular substances. Under mixtures with other substances there may for example be understood mixtures which cement. Formulations are, for example, flush pastes with organic liquids or pastes or fine pastes containing water, dispersing agents and, optionally, preservatives. The term paint represents, for example, physically or oxidatively drying lacquers, stoving lacquers, reactive lacquers, two-component lacquers, emulsion paints for weather-resistant coatings, and distempers. Printing inks are to be understood as those for printing paper, textiles and tinplate. They are also particularly suitable for pigmenting macromolecular organic substances. The macromolecular substances may be of natural origin, such as rubber, or may be obtained by chemical modification, such as acetylcellulose, cellulose butyrate or viscose, or may be produced synthetically, such as polymerisation products, polyaddition products and polycondensates. Plastic compositions such as polyvinyl chloride, polyvinyl acetate, polyvinyl propionate, polyolefins, for example polyethylene or polypropylene, polyesters, for example polyethylene terephthalate, polyamides, high molecular weight polyamides, polymers and copolymers of acrylic esters, methacrylic esters, acrylonitrile, acrylamide, butadiene and styrene, and polyurethanes and polycarbonates, may be mentioned. The materials pigmented with the products claimed can be in any desired form.

The pigments IV according to the invention furthermore have excellent fastness to water, oil, acid, lime, alkali, solvents, overlacquering, overspraying, sublimation, heat and vulcanisation, have a very high tinctorial strength and possess good dispersibility in plastic compositions.

EXAMPLE 1

40 g of aniline and 96 g of the quinazolinonyl-acetic acid ester of the formula

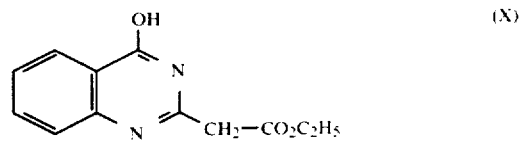

are added to 700 ml of 1,2-dichlorobenzene and the mixture is stirred for 6 hours at 170°-180° C. The alcohol formed is distilled off at the same time. After cooling, the product is filtered off, rinsed with 1,2-dichlorobenzene and methanol and dried at 80° C.

113 g (98% of theory) of the compound of the formula

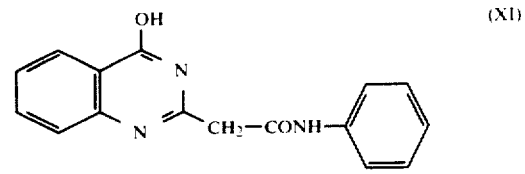

are obtained as a crystalline, white powder having a melting point above 260° C.

| | | | |
|---|---|---|---|
| Calculated: | C 68.6 | H 4.7 | N 15.1 |
| Found: | C 68.5 | H 4.8 | N 15.1 |

Further coupling components, having the structures indicated in the table which follows, are obtained in accordance with the process described in Example 1, if instead of aniline substituted anilines are used and instead of the quinazolinonyl-acetic acid ester (X) substituted quinazolinonyl-acetic acid esters are employed.

TABLE 1

[Structure: Quinazolinone with R1-R4 on left benzene ring, OH at position, linked via CH2-CONH to phenyl ring with R5-R8]

| Example | R1 | R2 | R3 | R4 | R5 | R6 | R7 | R8 |
|---------|----|----|----|----|----|----|----|----|
| 2 | H | H | H | H | Cl | H | H | H |
| 3 | H | H | H | H | C'$_3$ | H | H | H |
| 4 | H | H | H | H | OCH$_3$ | H | H | H |
| 5 | H | H | H | H | H | H | Cl | H |
| 6 | H | H | H | H | Cl | H | Cl | H |
| 7 | H | H | H | H | H | H | CH$_3$ | H |
| 8 | H | H | H | H | Cl | H | H | Cl |
| 9 | H | H | H | H | H | H | NHCOCH$_3$ | H |
| 10 | H | NO$_2$ | H | H | CH$_3$ | H | H | H |
| 11 | H | Br | H | H | Cl | H | H | H |
| 12 | H | Cl | H | Cl | Cl | H | NO$_2$ | H |
| 13 | Cl | Cl | Cl | Cl | OCH$_3$ | H | H | H |
| 14 | H | H | CH$_3$ | H | H | H | CN | H |
| 15 | H | H | OCH$_3$ | H | H | CF$_3$ | H | H |
| 16 | H | H | CF$_3$ | H | H | H | NHCOCH$_3$ | H |
| 17 | H | H | SO$_2$CH$_3$ | H | H | F | H | H |
| 18 | H | H | phthalimido (–N(CO)$_2$C$_6$H$_4$) | H | H | H | CH$_3$ | H |
| 19 | H | H | COOH | H | NO$_2$ | H | NHCOC$_6$H$_5$ | H |
| 20 | H | H | CN | H | H | H | CONH$_2$ | H |
| 21 | H | H | CONHC$_6$H$_5$ | H | H | H | SO$_2$CH$_3$ | H |
| 22 | H | H | SO$_2$N(CH$_3$)$_2$ | H | H | H | OC$_2$H$_5$ | H |
| 23 | H | H | NHCOCH$_3$ | H | CH$_3$ | H | CH$_3$ | H |
| 24 | H | H | NHCOC$_6$H$_5$ | H | Cl | H | Cl | Cl |
| 25 | H | H | NHC$_6$H$_5$ | H | H | H | SO$_2$NH$_2$ | H |

The structures of the compounds thus prepared are confirmed by the elementary analyses and the mass sprectra.

EXAMPLE 26

In the process mentioned in Example 1, the use of 20 g of p-phenylenediamine instead of aniline results in 68 g (77% of theory) of the coupling component of the formula

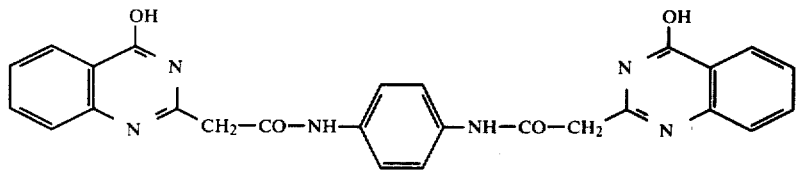

as a white powder having a melting point of >300° C. The structure is confirmed by elementary analysis and mass spectra.

EXAMPLE 27

12 g of the coupling component obtained according to Example 7 are stirred with 100 ml of 3% strength sodium hydroxide solution for 60 minutes at 20° C. The pH is then brought to 5 by adding glacial acetic acid, the mixture is cooled to 5° C. and a filtered diazonium salt solution obtained from 7.2 g of 2-nitro-4-chloroaniline is added dropwise. After stirring for a further 3 hours, the product is filtered off, washed until neutral and dried. 19.3 g (97% of theory) of the pigment of the formula

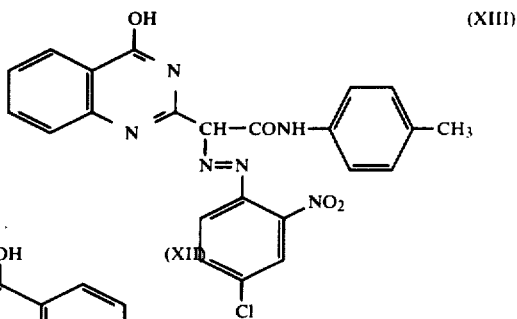

are obtained in yellow needles of melting point >300° C.

EXAMPLE 28

20 ml of concentrated H$_2$SO$_4$ and 22 g of 2-nitro-4-chloroaniline are added to 300 ml of dimethylformamide. After cooling to 10° C., the mixture is diazotised by adding a solution of 17 g of amyl nitrite in 300 ml of dimethylformamide, and a suspension of 50 g of the compound obtained according to Example 5, in 100 ml of dimethylformamide, is stirred in. Stirring is continued for 3 hours at 25° C. and the product is filtered off, washed with dimethylformamide and methanol and dried.

54 g (95% of theory) of the yellow pigment of the formula

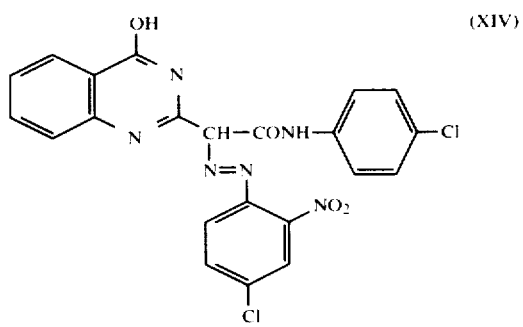

having a melting point >300° C. are thus obtained.

EXAMPLE 29

15 g of 1-amino-anthraquinone and 23 g of the compound obtained according to Example 2 are added to a mixture of 200 ml of nitrobenzene and 30 ml of 85% strength formic acid. The mixture is stirred for 30 minutes at room temperature and a solution of 6 g of NaNO₂ in 10 ml of water is then added dropwise. After 2 hours, the batch is heated in vacuo to remove water, the residual mixture is heat-treated for 1 hour at 150° C. and the product is filtered off at 50° C. It is rinsed with nitrobenzene, methanol and water, and dried.

29.5 g (80% of theory) of the yellow pigment of the formula

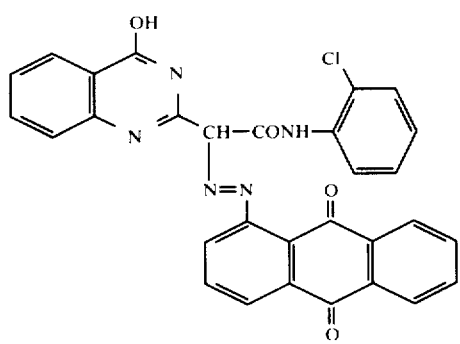

of melting point >300° C. are obtained.

Further pigments, having the colour shades indicated in Table 2 below are obtained in accordance with the process mentioned in Example 16 if instead of 2-nitro-4-chloroaniline the diazo components indicated in the second column, and instead of the coupling component from Example 5 the coupling components indicated in the third column, are used.

TABLE 2

| Example | Diazo component | Coupling component | Colour shade |
|---|---|---|---|
| 30 | NH₂, Cl, Cl (2,6-dichloroaniline) | Example 2 | greenish-tinged yellow |
| 31 | NH₂, F (3-fluoroaniline) | Example 5 | greenish-tinged yellow |
| 32 | NH₂, CF₃ (3-trifluoromethylaniline) | Example 4 | yellow |
| 33 | NH₂, Cl (2-chloroaniline) | Example 14 | yellow |
| 34 | NH₂, CH₃ (2-methylaniline) | Example 23 | yellow |
| 35 | NH₂ (4-substituted aniline) | Example 18 | yellow |
| 36 | NH₂, OC₂H₅, NHCOCH₃ | Example 16 | yellow |
| 37 | NH₂, NH-CO-(3-NO₂-phenyl) | Example 3 | yellow |
| 38 | NH₂, NO₂, NHCOCH₃ | Example 14 | yellow |
| 39 | NH₂, COOH | Example 22 | greenish-tinged yellow |
| 40 | NH₂, CO₂CH₃ | Example 24 | yellow |
| 41 | NH₂, CN | Example 21 | greenish-tinged yellow |
| 42 | NH₂, CN, Cl | Example 9 | greenish-tinged yellow |
| 43 | NH₂, Cl, H₂NOC | Example 25 | yellow |

TABLE 2-continued

| Example | Diazo component | Coupling component | Colour shade |
|---|---|---|---|
| 44 | 4-aminobenzanilide (NH2-C6H4-CONHC6H5) | Example 17 | yellow |
| 45 | 4-amino-phenyl methyl sulfone (NH2-C6H4-SO2CH3) | Example 20 | yellow |
| 46 | 4-amino-benzenesulfonamide (NH2-C6H4-SO2NH2) | Example 9 | yellow |
| 47 | 3,3'-dichlorobenzidine | Example 3 | yellow |
| 48 | 2-aminobenzothiazole | Example 10 | orange |
| 49 | (anthranilic acid derivative with NH2) | Example 5 | yellow |
| 50 | 1-amino-5-benzoylamino-anthraquinone | Example 6 | orange |
| 51 | 2-aminoanthraquinone | Example 5 | yellow |
| 52 | 1-amino-5-chloro-anthraquinone | Example 2 | yellow |
| 53 | 1-amino-5-nitro-anthraquinone | Example 7 | yellow |
| 54 | 1-amino-4-chloro-anthraquinone | Example 9 | yellow |
| 55 | 1-amino-2-methyl-anthraquinone | Example 2 | yellow |
| 56 | 1-amino-2-carboxy-anthraquinone | Example 2 | yellow |
| 57 | 1-amino-8-benzoyloxycarbonylamino-anthraquinone | Example 3 | reddish-tinged yellow |
| 58 | 1-amino-4-benzoylamino-anthraquinone | Example 4 | brown |
| 59 | 1-amino-4-(4-chlorobenzoylamino)-anthraquinone | Example 4 | brown |
| 60 | 1,5-diamino-anthraquinone | Example 7 | orange |
| 61 | 1-amino-anthrapyridone derivative | Example 2 | yellow |

EXAMPLE 62

(a) 8 g of the finely divided pigment obtained according to Example 28 are ground with a stoving lacquer, consisting of 25 g of coconut oil alkyd resin (40% of coconut oil), 10 g of melamine resin, 50 g of toluene and 7 g of glycol monomethyl ether, on an automatic Hoover-Muller grinder. The mixture is applied to the substrate to be lacquered, the lacquer is cured by stoving at 130° C., and yellow lacquerings having very good fastness to overlacquering and excellent fastness to light and weathering are obtained.

Pigmented stoving lacquers with equal fastness characteristics are obtained if 15–25 g of the stated alkyd resin or of an alkyd resin based on cottonseed oil, dehydrated castor oil, castor oil or synthetic fatty acids are used and instead of the stated amount of melamine resin 10–15 g of the melamine resin mentioned or of a condensation product of formaldehyde with urea or with benzoguanamine are employed.

(b) If instead of the stated amount of pigment, 1 to 10 g of a mixture of titanium oxide (rutile type) with the pigment mentioned in Example 62 a, in the ratio of 0.5–50:1, are ground into the lacquer mentioned in Example 62 a, and the material is processed further in the same manner, lacquerings which have equal fastness characteristics and have a yellow colour shade displaced towards white with increasing titanium dioxide content, are obtained.

EXAMPLE 63

6 g of finely divided pigment according to Example 28 are ground into 100 g of a nitrocellulose lacquer which consists of 44 g of collodion cotton (low viscosity, moist with 35% of butanol), 5 g of dibutyl phthalate, 40 g of ethyl acetate, 20 g of toluene, 4 g of n-butanol and 10 g of glycol monomethyl ether. After brushing out and drying, yellow lacquerings having excellent fastness to light and to overlacquering are obtained. The same results are obtained when using nitro lacquers containing 10–15 g of nitrocellulose, 5–10 g of plasticiser and 70–85 g of a solvent mixture, preferably using aliphatic esters, such as ethyl acetate or butyl acetate, and aromatics, such as toluene and xylene, and minor proportions of aliphatic ethers such as glycol ethers, and alcohols, such as butanol. By plasticisers there may for example be understood phthalic acid esters, such as dioctyl phthalate and dibutyl phthalate, esters of phosphoric acid, castor oil by itself or castor oil in combination with oil-modified alkyd resins.

Lacquerings with similar fastness characteristics are obtained when using other physically drying spirit lacquers, Zapon lacquers and nitro lacquers, air-drying oil, synthetic resin and nitro combination lacquers, and stoving and air-drying epoxide resin lacquers, optionally in combination with urea resins, melamine resins, alkyd resins or phenolic resins.

EXAMPLE 64

5 g of pigment according to Example 28, brought to a finely divided state, are ground into 100 g of a paraffin-free drying unsaturated polyester resin in a porcelain ball mill. 10 g of styrene, 59% of melamine-formaldehyde resin and 1 g of a paste consisting of 40 g of cyclohexanone peroxide and 60% of dibutyl phthalate are thoroughly stirred with the ground material and finally 4 g of a drier solution (10% strength cobalt naphthenate in white spirit) and 1 g of a silicone oil solution (1% strength in xylene) are admixed. The mixture is applied to primed wood and a very glossy, water-resistant and weathering-fast yellow lacquering of excellent lightfastness is obtained.

If instead of the reactive lacquer based on unsaturated polyester resins, amine-curing epoxide resin lacquers with dipropylenediamine as the amino component are used, yellow lacquerings of excellent fastness to weathering and to efflorescence are obtained.

EXAMPLE 65

100 g of a 65% strength solution of an aliphatic polyester, containing about 8% of free hydroxyl groups, in glycol monoethyl ether acetate, are ground with 5 g of the pigment obtained according to Example 29 and the batch is then thoroughly mixed with 44 g of a 67% strength solution of the reaction product of 1 mol of trimethylolpropane with 3 mols of toluylene-diisocyanate. There is no impairment of the drip time and after application of the mixture and reaction of the components very glossy yellow polyurethane lacquerings of excellent fastness to efflorescence, light and weathering are obtained.

Pigmentations with similar fastness characteristics are obtained when using other two-component lacquers based on aromatic or aliphatic isocyanates and on polyethers or polyesters containing hydroxyl groups, and also when using moisture-drying polyisocyanate lacquers which give polyurea lacqerings.

EXAMPLE 66

5 g of a fine paste, obtained by kneading 50 g of the pigment, obtained according to Example 24, with 15 g of an aryl polyglycol ether emulsifier and 35 g of water, are mixed with 10 g of baryte as the filler, 10 g of titanium dioxide (rutile type) as a white pigment and 40 g of an aqueous emulsion paint containing about 50% of polyvinyl acetate. The paint is brushed out and after drying yellow paint films having very good fastness to lime and cement and excellent fastness to weathering and light are obtained.

The fine paste obtained by kneading is equally suitable for pigmenting clear polyvinyl acetate emulsion paints, emulsion paints containing copolymers of styrene and maleic acids as the binder, and emulsion paints based on polyvinyl propionate, polymethacrylate or butadiene-styrene.

EXAMPLE 67

10 g of the pigment paste mentioned in Example 66 are mixed with a mixture of 5 g of chalk and 5 g of 20% strength glue solution. A yellow wallpaper paint is obtained, which gives coatings of excellent lightfastness. Other non-ionic emulsifiers, such as the reaction products of nonylphenyol with ethylene oxide, or ionic wetting agents, such as the sodium salts of alkylarylsulphonic acid, for example of dinaphthylmethanedisulphonic acid, sodium salts of substituted sulpho-fatty acid esters and sodium salts of paraffin sulphonic acids, in combination with alkyl polyglycol ethers, can also be used to prepare the pigment paste.

EXAMPLE 68

A mixture of 65 g of polyvinyl chloride, 35 g of diisooctyl phthalate, 2 g of dibutyl-tin mercaptide, 0.5 g of titanium dioxide and 0.5 g of the pigment of Example 28 are colour-compounded on a mixing mill at 165° C. An intensely yellow composition is obtained, which can be used for the manufacture of films or mouldings. The colouration is distinguished by excellent lightfastness and very good fastness to plasticisers.

EXAMPLE 69

0.2 g of pigment according to Example 28 are mixed with 100 g of polyethylene granules, polypropylene granules or polystyrene granules. The mixture can either be directly moulded on an injection moulding machine at 220° to 280° C., or be converted to coloured rods on an extruder or to coloured hides on a mixing mill. If desired, the rods or hides are granulated and the granules moulded in an injection moulding machine.

The yellow mouldings have very good lightfastness and fastness to migration. In a similar manner, synthetic polyamides obtained from caprolactam or from adipic acid and hexamethylenediamine, or the condensates of terephthalic acid and ethylene glycol, can be coloured at 280°–300° C., if necessary under a nitrogen atmosphere.

EXAMPLE 70

1 g of pigment according to Example 28, 10 g of titanium dioxide (rutile type) and 100 g of a pulverulent copolymer based on acrylonitrile-butadiene-styrene are mixed and colour-compounded on a mixing mill at 140°–180° C. A yellow hide is obtained, which is granulated, and the granules are moulded in an injection moulding machine at 200°–250° C. Yellow mouldings having very good lightfastness and fastness to migration, and excellent heat resistance, are obtained.

Plastics based on cellulose acetate, cellulose butyrate and their mixtures are coloured in a similar manner, but at temperatures of 180°–220° C. and without addition of titanium dioxide, to give colourations having similar fastness characteristics.

EXAMPLE 71

0.2 g of pigment according to Example 28, in a finely divided form, are mixed with 100 g of a polycarbonate-based plastic in an extruder or in a kneading screw at 250°–280° C., and the mixture is converted to granules. Yellow, transparent granules of excellent lightfastness and heat resistance are obtained.

EXAMPLE 72

90 g of a slightly branched polypropylene glycol having a molecular weight of 2,500 and a hydroxyl number of 56, 0.25 g of endoethylenepiperazine, 0.3 g of tin-(II) octoate, 1.0 g of a polyether-siloxane, 3.5 g of water and 12.0 g of a ground paste of 10 g of pigment according to Example 29 in 50 g of the stated polypropylene glycol are thoroughly mixed with one another and then intimately mixed with 45 g of toluylene-diisocyanate (80% of 2,4-isomer and 20% of 2,6-isomer), and poured into a mould. The mixture becomes turbid after 6 seconds, and the formation of a foam takes place. After 70 seconds, an intensely yellow, soft polyurethane foam has formed; its pigmentation exhibits excellent lightfastness.

EXAMPLE 73

90 g of a slightly branched polyester obtained from adipic acid, diethylene glycol and trimethylolpropane and having a molecular weight of 2,000 and a hydroxyl number of 60 are mixed with the following components: 1.2 g of dimethylbenzylamine, 2.5 g of sodium castor oil-sulphate, 2.0 g of an oxyethylated, benzylated hydroxydiphenyl, 1.75 g of water and 12 g of a paste prepared by grinding 10 g of the pigment according to Example 28 into 50 g of the above-mentioned polyester. After mixing, 40 g of toluylene-diisocyanate (65% of 2,4-isomer and 35% of 2,6-isomer) are stirred in whilst stirring and the mixture is poured into a mould and foamed. After 60 seconds, a yellow, soft polyurethane foam has formed, the colouration of which is distinguished by very good lightfastness characteristics.

EXAMPLE 74

Yellow offset prints of high balance and colour intensity, and very good lightfastness and fastness to lacquering, are obtained with a printing ink prepared by grinding 35 g of pigment according to Example 28 and 65 g of linseed oil, and adding 1 g of drier (Co naphthenate, 50% strength in white spirit). The use of this printing ink in letterpress, collotype or lithographic printing, or printing from engraved steel plates, leads to yellow prints having similar fastness characteristics. If the pigment is used for colouring tinplate printing inks or low viscosity gravure printing pastes or printing inks, yellow prints having similar fastness characteristics are obtained.

EXAMPLE 75

A printing paste is prepared from 10 g of the fine pigment paste mentioned in Example 66, 100 g of 3% strength tragacanth, 100 g of an aqueous 50% strength egg albumin solution and 25 g of a non-ionic wetting agent. A textile fibre fabric is printed and then steamed at 100° C., and a yellow print which is distinguished by excellent fastness characteristics, especially lightfastness characteristics, is obtained. Instead of the tragacanth and egg albumin, other binders usable for fixing to the fibres, for example binders based on synthetic resins, British gum or cellulose glycolate, can be used in the printing mixture.

EXAMPLE 76

A mixture of 100 g of pale crepe, 2.6 g of sulphur, 1 g of stearic acid, 1 g of mercaptobenzthiazole, 0.2 g of hexamethylenetetramine, 5 g of zinc oxide, 60 g of chalk and 2 g of titanium dioxide (anatase type) is coloured with 2 g of the pigment obtained according to Example 28 on a mixing mill at 50° C. and is then vulcanised for 12 minutes at 140° C. A yellow vulcanised product of very good lightfastness is obtained.

EXAMPLE 77

100 g of a 20% strength aqueous paste of the pigment according to Example 28, for example prepared by dissolving the colorant in 96% strength sulphuric acid, pouring the solution out onto ice, filtering off the product and washing it with water until neutral, are added to 22.5 l of an aqueous, approximately 9% strength, viscose solution in a stirred mixing vessel. The coloured composition is stirred for 15 minutes, then deaerated, and subjected to a spinning and desulphurisation process.

Yellow filaments or films having very good lightfastness are obtained.

EXAMPLE 78

10 kg parts of a paper pulp containing 4 g of cellulose per 100 g, are treated for about 2 hours in a hollander. During this time, the following are added at intervals of quarter of an hour: 4 g of resin size, thereafter 30 g of an approximately 15% strength pigment dispersion obtained by grinding 4.8 g of the pigment obtained according to Example 28 with 4.8 g of dinaphthylmethanedisulphonic acid and 22 g of water in a ball mill, and thereafter 5 g of aluminium sulphate.

After finishing on a papermaking machine, a yellow paper of excellent lightfastness is obtained.

EXAMPLE 79

The yellow-pigmented paper prepared according to Example 78 is impregnated with a 55% strength solution of a urea-formaldehyde resin in n-butanol and baked at 140° C. A yellow laminate paper having very good fastness to migration and excellent lightfastness is obtained.

A laminate paper with similar fastness properties is obtained by laminating a paper which has been gravure-printed with a printing ink which contains the yellow fine pigment paste described in Example 66 and water-soluble or saponifiable binders.

EXAMPLE 80

20 parts of the pigment obtained according to Example 28 are predispersed in 50 parts of dimethylformamide in a dissolver, and are then drowned in a bead mill with the optional addition of a dispersing auxiliary and of 50 parts of a 10% strength polyacrylonitrile solution in dimethylformamide. The pigment composition is then added in portions, in accordance with known methods, to a polyacrylonitrile spinning solution, and the batch is homogenised and spun to form filaments in accordance with a dry or wet spinning process customary and known in the art.

The colourations thus obtained exhibit very good brilliance and fastness to rubbing, migration, heat, light and weathering.

We claim:

1. An azo colorant of the formula

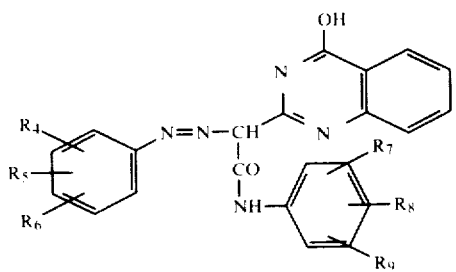

wherein $R_4$ represents hydrogen, halogen, $C_1$-$C_4$-alkyl, $C_1$-$C_4$-alkoxy, nitro, cyano, carboxyl, $C_1$-$C_4$-alkylsulphonyl, trifluoromethyl, $C_1$-$C_4$-alkylcarbonylamino, benzoylamino which is unsubstituted or substituted by $C_1$-$C_4$ alkyl, $C_1$-$C_4$-alkoxy, fluorine, chlorine, bromine or nitro, $C_1$-$C_4$-alkoxycarbonyl, carbamoyl or sulphamoyl which are unsubstituted or monosubstituted or disubstituted by $C_1$-$C_4$-alkyl, phenyl or benzyl, said phenyl and benzyl being unsubstituted or substituted by $C_1$-$C_4$-alkyl, $C_1$-$C_4$-alkoxy, fluorine, chlorine, bromine and nitro, $C_1$-$C_4$-alkylsulphonylamino, and phenylsulphonylamino which is unsubstituted or substituted by $C_1$-$C_4$-alkyl, $C_1$-$C_4$-alkoxy, fluorine, chlorine, bromine or nitro, $R_5$ represents hydrogen, halogen, $C_1$-$C_4$-alkyl, cyano, $C_1$-$C_4$-alkoxy, nitro or trifluoromethyl, $R_6$ represents hydrogen, chlorine, $C_1$-$C_4$-alkyl or $C_1$-$C_4$-alkoxy, $R_7$ represents hydrogen, halogen, $C_1$-$C_4$-alkyl, $C_1$-$C_4$-alkoxy, nitro, cyano, $C_1$-$C_4$-alkylsulphonyl, trifluoromethyl, $C_1$-$C_4$-alkylcarbonylamino, benzoylamino which is unsubstituted or substituted by $C_1$-$C_4$-alkyl, $C_1$-$C_4$-alkoxy, fluorine, chlorine, bromine or nitro, $C_1$-$C_4$-alkoxycarbonyl, or carbamoyl or sulphamoyl which are unsubstituted or monosubstituted or disubstituted by $C_1$-$C_4$-alkyl, phenyl or benzyl, said phenyl and said benzyl each being unsubstituted or said phenyl and said benzyl is substituted by $C_1$-$C_4$-alkyl, $C_1$-$C_4$-alkoxy, fluorine, chlorine, bromine and nitro, $R_8$ represents hydrogen, halogen, $C_1$-$C_4$-alkyl, cyano, $C_1$-$C_4$-alkoxy, nitro or trifluoromethyl and $R_9$ represents hydrogen, chlorine, $C_1$-$C_4$-alkyl, $C_1$-$C_4$-alkoxy, or a radical of the formula

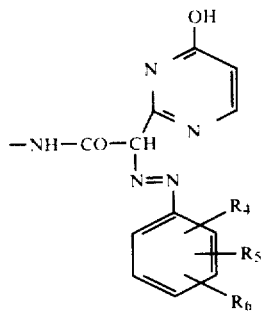

wherein $R_4$, $R_5$ and $R_6$ have the above-mentioned meanings.

2. An azo colorant of the formula

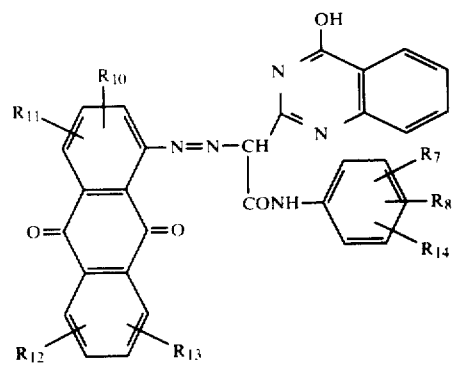

in which $R_7$ represents hydrogen, halogen, $C_1$-$C_4$-alkyl, $C_1$-$C_4$-alkoxy, nitro, cyano, $C_1$-$C_4$-alkylsulphonyl, trifluoromethyl, $C_1$-$C_4$-alkylcarbonylamino, benzoylamino which is unsubstituted or substituted by $C_1$-$C_4$-alkyl, $C_1$-$C_4$-alkoxy, fluorine, chlorine, bromine or nitro, $C_1$-$C_4$-alkoxy-carbonyl, or carbamoyl or sulphamoyl which are unsubstituted or monosubstituted or disubstituted by $C_1$-$C_4$-alkyl, phenyl or benzyl, each of said phenyl and benzyl being unsubstituted or substituted by $C_1$-$C_4$-alkyl, $C_1$-$C_4$-alkoxy, fluorine, chlorine, bromine and nitro, $R_8$ represents hydrogen, halogen, $C_1$-$C_4$-alkyl, cyano, $C_1$-$C_4$-alkoxy, nitro or trifluoromethyl and $R_{10}$, $R_{11}$, and $R_{12}$ and $R_{13}$ represent hydrogen, chlorine, bromine, carboxyl, $C_1$-$C_4$-alkoxycarbonyl, carboxamide, $C_1$-$C_4$-alkylcarbonylamino, benzoylamino which is unsubstituted or substituted by 1 or 2 nitro or 1 or 2 chlorine or bromine, $C_1$-$C_4$-alkylsulphonylamino or phenylsulphonylamino which is unsubstituted or substituted by methyl, methoxy or chlorine and, $R_{14}$ represents hydrogen, chlorine, $C_1$-$C_4$-alkyl, $C_1$-$C_4$-alkoxy or the radical of the formula

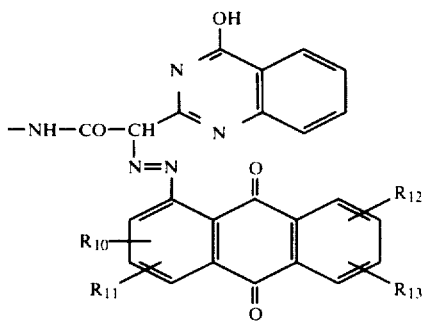

wherein $R_{10}$–$R_{13}$ have the abovementioned meanings.

3. An azo colorant of the formula

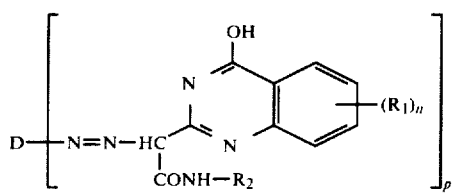

wherein $R_1$ represents halogen, alkyl, nitro, alkylsulphonylamino, alkylcarbonylamino, $C_1$–$C_4$ alkoxy, trifluoromethyl, phthalimidyl, carboxyl, cyano, carbamoyl, sulphamoyl, benzoylamino, arylamino and arylsulphonylamino, said carbamoyl and sulphamoyl groups each being unsubstituted or substituted by $C_1$–$C_4$ alkyl, phenyl which phenyl, in turn, is unsubstituted or substituted by $C_1$–$C_4$ alkyl, $C_1$–$C_4$-alkoxy, fluorine, chlorine, bromine, phthalimidyl, nitro or substituted by benzyl, said benzoylamino being unsubstituted or substituted in the benzene nucleus by chlorine, $C_1$–$C_4$ alkyl, $C_1$–$C_4$ alkoxy or nitro, said aryl amino being unsubstituted or substituted by $C_1$–$C_4$ alkyl, $C_1$–$C_4$ alkoxy, fluorine, chlorine, bromine or nitro, said arylsulphonylamino being unsubstituted or substituted by $C_1$–$C_4$ alkyl, $C_1$–$C_4$ alkoxy, fluorine, chlorine, bromine or nitro;

$R_2$ denotes an unsubstituted phenyl radical or a phenyl radical carrying 1–5 substituents of the group chlorine, bromine, fluorine, $C_1$–$C_4$ alkyl, $C_1$–$C_4$ alkoxy, nitro, trifluoromethyl, cyano, carboxyl, $C_1$–$C_4$ alkoxycarbonyl, or $R_2$ represents unsubstituted carbamoyl, sulphamoyl, acylamino, arylamino, alkylsulphonylamino or aryl sulphonylamino or carbamoyl sulphamoyl, acylamino, arylamino, alkylsulphonylamino, or arylsulphonylamino radicals substituted with the substituents for $R_1$ or $R_2$ represents a phthalimidyl group or a radical of the formula

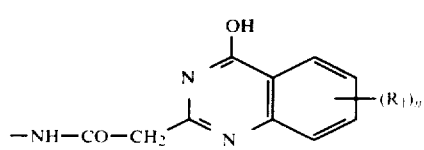

n denotes 0, 1, 2, 3 or 4;
p denotes an integer and

D denotes a radical of a compound of an aromatic or heterocyclic aromatic amine of the group consisting of aniline, 2-methylaniline, 2,4-dimethylaniline, 2-nitroaniline, 3-nitroaniline, 4-nitroaniline, 2,4-dinitroaniline, 2-chloro-4-nitroaniline, 4-chloro-2-nitroaniline, 2-chloro-5-nitroaniline, 2-nitro-4-methylaniline, 2-methyl-4-nitroaniline, 2-methyl-5-nitroaniline, 4-methoxy-2-nitroaniline, 2-cyano-4-nitroaniline, 2-bromo-4-nitroaniline, 2-nitro-4-methylsulphonylaniline, 2-nitro-4-ethylsulphonylaniline, 2-chloroaniline, 4-chloroaniline, 2,4-dichloroaniline, 2,5-dichloroaniline, 2,6-dichloroaniline, 3,4-dichloroaniline, 3,5-dichloroaniline, 2,4,5-trichloroaniline, 2,4,6-trichloroaniline, 2-cyano-5-chloroaniline, 2-methyl-4-chloroaniline, 2-methyl-5-chloroaniline, 2,4-dichloro-5-ethylaniline, 2,5-dichloro-4-methylaniline, 2-chloro-4-methylsulphonylaniline, 2-cyano-5-chloroaniline, 2,4-dichloro-5-methoxyaniline, 2-chloro-5-trifluoromethylaniline, 4-chloro-2-trifluoromethylaniline, 3,5-bis-trifluoromethylaniline, 2,4-dimethoxyaniline, 2,5-dimethoxyaniline, 2,5-diethoxyaniline, 2,4-dimethoxy-5-chloroaniline, 2,5-dimethoxy-4-chloroaniline, 2-methoxy-5-methylaniline, 4-methoxy-2-methylaniline, 2-methoxy-5-methyl-4-chloroaniline, 2-methoxy-4-nitroaniline, 4-methoxy-2-nitroaniline, 2-methoxy-5-nitroaniline, 2,5-dimethoxy-4-nitroaniline, 2-methoxy-5-methyl-4-nitroaniline, 2-methoxy-5-chloro-4-nitroaniline, 2-methoxy-5-ethylsulphonylaniline, 2-methoxy-5-phenylsulphenylaniline, 2-methoxy-5-benzylsulphonylaniline, 2-methoxy-4-chloroaniline, 2-ethoxy-4-chloroaniline, 2-methoxy-5-chloroaniline, 2-ethoxy-5-chloroaniline, 2-methoxy-4,5-dichloroaniline, 2-amino-5-chlorodiphenyl ether, 2-amino-4,4'-dichlorodiphenyl ether, 2-amino-4,6-dichlorodiphenyl ether, 4-amino-5-methoxybenzenesulphonic acid 4-nitrophenyl ester, 5-acetylamino-2-nitroaniline, 5-acetylamino-2-chloro-5-methylaniline, 4-acetylamino-2,5-dichloroaniline, 5-acetylamino-2,4-dichloroaniline, 4-benzoylamino-2-methyl-5-methoxyaniline, 5-benzoylamino-2-chloroaniline, 4-benzoylamino-2-chloro-5-methoxyaniline, 2-amino-benzoic acid methyl ester, 2-aminobenzoic acid ethyl ester, 2-aminobenzoic acid isobutyl ester, 4-chloro-2-amino-benzoic acid methyl ester, 5-chloro-2-aminobenzoic acid methyl ester, 6-chloro-2-aminobenzoic acid methyl ester, 3,5-dichloro-2-aminobenzoic acid methyl ester, 4,6-dichloro-2-aminobenzoic acid methyl ester, 5-bromo-2-aminobenzoic acid methyl ester, 4-nitro-2-aminobenzoic acid methyl ester, 5-nitro-2-aminobenzoic acid methyl ester, 4-methyl-2-aminobenzoic acid methyl ester, 5-methyl-2-aminobenzoic acid methyl ester, 6-methyl-2-aminobenzoic acid methyl ester, 4-trifluoromethyl-2-aminobenzoic acid methyl ester, 4-methoxy-2-aminobenzoic acid methyl ester, 4-methoxy-3-aminobenzoic acid phenyl ester, 4-carbamoyl-2-aminobenzoic acid methyl ester, 4-acetylamino-2-aminobenzoic acid methyl ester, 4-benzoylamino-2-aminobenzoic acid methyl ester, 4-(2,5-dichlorobenzoylamino)-2-aminobenzoic acid methyl ester, 4-sulphamoyl-2-aminobenzoic acid methyl ester, 2-aminonaphthalene-3-carboxylic acid methyl ester, 4-methyl-3-aminobenzoic acid methyl ester, 1-aminobenzene-2,5-dicarboxylic acid dimethyl ester, 1-aminobenzene-3,5-dicarboxylic acid dimethyl ester, 2-aminobenzamide, 4-aminobenzamide, 4-chloro-3-aminobenzamide, 4,6-dichloro-3-aminobenzamide, 3-amino-4-methoxy-benzamide, 3-amino-4-methoxybenzoic acid phenylamide, 3-amino-4-methylbenzoic acid methylamide, 3-amino-4-methylbenzoic acid 2,4-dimethylphenyl-amide, 1-aminobenzene-3,5-dicarboxylic acid diamide, 3-amino-4-methylbenzoic acid 2,5-dichlorophenyl-amide, 3-amino-4-methoxycarbonylbenzamide, 3-amino-4-methoxycarbonylbenzoic acid phenylamide, 3-amino-4-methoxycarbonylbenzoic acid 2,5-dichlorophenyl-amide, 3-amino-4-methoxybenzenesulphonic acid methylamide, 3-amino-4-methoxybenzenesulphonic acid diethylamide, 2,5-dimethoxy-4-aminobenzenesulphonic acid methylamide, 2-methyl-5-methoxy-4-aminobenzenesulphonic acid methylamide, 3-amino-4-methylbenzenesulphonic acid phenylamide, 4-amino-2,5-dimethoxybenzenesulphonic acid methylamide, 4-amino-2-methyl-5-methoxybenzenesulphonic acid methylamide, 2-chloro-1-aminonaphthalene, 1-amino-2-methoxynaphthalene, 1-amino-4-nitronaphthalene, 2-amino-5-nitronaphthalene, 2-aminothiazole, 2-amino-4-methylthiazole, 2-amino-5-chlorothiazole, 2-amino-5-nitrothiazole, 2-amino-4-methylthiazole-5-carboxylic acid methyl ester, 2-amino-4-methylthiazole-5-carboxylic acid dimethylamide, 2-aminobenzthiazole, 2-amino-6-methylbenzthiazole, 2-amino-5-methoxybenzthiazole, 2-amino-6-methoxybenzthiazole, 2-amino-6-chlorobenzthiazole, 2-amino-6-methylsulphonylbenzthiazole, 6-methyl-2-(4-aminophenyl)-benzthiazole, 5-amino-3-phenyl-1,2,4-thiadiazole, 2-amino-4-methylcarbostyril, 6-amino-4-methyl-2-chlorocarbostyril, 3-amino-4-methoxybenzoxazole, 6-amino-2,4-dihydroxyquinazoline, 1-aminoanthraquinone, 2-aminoanthraquinone, 1-amino-2-chloroanthraquinone, 1-amino-4-chloroanthraquinone, 1-amino-5-chloroanthraquinone, 1-amino-6-chloroanthraquinone, 1-amino-6(7)-chloroanthraquinone (mixture), 1-amino-5,8-dichloroanthraquinone, 1-amino-2-bromoanthraquinone, 1-amino-2,4-dibromoanthraquinone, 1-amino-6,7-dichloroanthraquinone, 1-amino-6-fluoroanthraquinone, 1-amino-7-fluoroanthraquinone, 1-amino-6,7-difluoroanthraquinone, 2-amino-1-chloroanthraquinone, 2-amino-3-chloroanthraquinone, 2-amino-3-bromoanthraquinone, 1-amino-4-nitroanthraquinone, 1-amino-5-nitroanthraquinone, 1-amino-2-methylanthraquinone, 1-amino-2-methyl-4-chloroanthraquinone, 1-amino-2-methyl-4-bromoanthraquinone, 1-aminoanthraquinone-2-carboxylic acid, 1-aminoanthraquinone-2-carboxylic acid amide, 1-aminoanthraquinone-2-carboxylic acid methyl ester, 1-amino-4-nitroanthraquinone-2-carboxylic acid, 1-amino-2-acetylanthraquinone, 1-amino-4-acetylaminoanthraquinone, 1-amino-5-acetylaminoanthraquinone, 1-amino-5-benzoylaminoanthraquinone, 1-amino-4-benzoylaminoanthraquinone, 1-amino-8-benzoylaminoanthraquinone, 1-amino-4-hydroxyanthraquinone, 1-amino-5-hydroxyanthraquinone, 1-amino-4-methoxyanthraquinone, 1-amino-2-methoxy-4-hydroxyanthraquinone, 1-amino-4-methylaminoanthraquinone, 1-amino-4-benzylaminoanthraquinone, 1-amino-4-cyclohexylaminoanthraquinone, 1-amino-4-anilinoanthraquinone, 1-amino-2-bromo-4-methylmercaptoanthraquinone, 1-amino-4-(4-methylphenylsulphonylamino)-2-phenylthioanthraquinone, 1-amino-6-methylmercaptoanthraquinone, 2-phenyl-6-amino-4,5-phthaloylbenzimidazole, 6-chloro-2-amino-3,4-phthaloylacridone, 7-chloro-2-amino-3,4-phthaloylacridone, 5-chloro-8-amino-3,4-phthaloylacridone, 3-aminobenzanthrone, 5-aminopyrazoleanthrone, 4-aminoanthrapyrimidine, 6-aminoanthrapyrimidine, 6-amino-3-methylanthrapyridone, 7-amino-3-methylanthrapyridone, 1,5-diaminoanthraquinone, 1,4-diaminoanthraquinone, 1,8-diaminoanthraquinone, 1,6-/1,7-diaminoanthraquinone (mixture), 2,6-diaminoanthraquinone, 1,5-diamino-4-chloroanthraquinone, 1,4-diamino-5-nitroanthraquinone, 1,5-diamino-2,4,6,8-tetrabromoanthraquinone, 1,5-diamino-4,8-dihydroxyanthraquinone, 1,8-diamino-4,5-dihydroxyanthraquinone, 4,4'-diamino-1,1'-dianthrimide and 1-amino-2-bromo-4-(4-methylphenylsulphonylamino)-anthraquinone, said radical being free from sulphonic acid groups.

4. An azo colorant according to claim 3, wherein $p = 1$ or 2.

* * * * *